United States Patent [19]
Chang et al.

[11] Patent Number: 6,140,119
[45] Date of Patent: *Oct. 31, 2000

[54] EXPRESSION OF ESTROGEN RECEPTORS IN TYPE I AND TYPE II HUMAN BREAST EPITHELIAL CELLS

[75] Inventors: Chia-Cheng Chang; James Trosko, both of Okemos, Mich.

[73] Assignee: Michigan State University, East Lansing, Mich.

[ * ] Notice: This patent is subject to a terminal disclaimer.

[21] Appl. No.: 08/790,659

[22] Filed: Jan. 29, 1997

Related U.S. Application Data

[60] Continuation-in-part of application No. 08/558,786, Nov. 16, 1995, Pat. No. 5,814,511, which is a division of application No. 08/308,118, Sep. 16, 1994, Pat. No. 5,650,317.

[51] Int. Cl.$^7$ .............................. C12N 5/00; C12N 5/02; C12N 5/08
[52] U.S. Cl. .......................... 435/371; 435/325; 435/366; 435/378
[58] Field of Search .................................... 435/371, 366, 435/325, 378

[56] References Cited

U.S. PATENT DOCUMENTS

| | | | |
|---|---|---|---|
| 4,411,990 | 10/1983 | Salmon et al. | 435/32 |
| 5,061,620 | 10/1991 | Tsukamoto et al. | 435/7.21 |
| 5,081,030 | 1/1992 | Civin | 435/240 |
| 5,087,570 | 2/1992 | Weissman et al. | 424/93.7 |
| 5,132,212 | 7/1992 | Kirsch et al. | 435/69.4 |
| 5,185,438 | 2/1993 | Lemischka | 536/23.2 |
| 5,214,133 | 5/1993 | Kirsch et al. | 530/399 |
| 5,226,914 | 7/1993 | Caplan et al. | 623/16 |
| 5,258,367 | 11/1993 | Bazer et al. | 514/6 |
| 5,270,458 | 12/1993 | Lemischka | 536/23.5 |
| 5,300,422 | 4/1994 | Gerson et al. | 435/4 |

OTHER PUBLICATIONS

"Contact Insensitivity of a Subpopulation of Normal Human Fetal Kidney Epithelial Cells and of Human Carcinoma Cell Lines", Chang, et al, *Cancer Research 47*, pp. 1634–1645, Mar. 15, 1987.
Whitehead et al., J. National Cancer Inst., 70:649–661, 1983.
Whitehead et al., J. National Cancer Inst., 73:643–648, 1984.
Kao et al., Carcinogenesis, 16:531–538, 1995.
Kang et al., Proc. Amer. Assoc. Cancer Res., 37:235, Abst. #1605, 1996.
Gronemeyer, H. (1991) Ann. Rev. Genetics 25, 89–123.
Dickson, R.B. & Lippman, M.E. (1994) in The Molecular Basis of Breast Cancer, eds. Mendelsohn, J., Howley, P.M., Israel, M.A., & Liotta, L.A., (W.B. Saunders Co., Philadelphia), pp. 358–384.
Lippman, M.E., and Allegra, J.C. (1980) Cancer 46, 2829–2834.
Manni, A., Arafah, B., and Pearson, O.H. (1980) Cancer 46, 2838–2841.
Jensen, E.V. (1981) Cancer 47, 2319–2326.
Iglehart, J.D. (1991) in: Textbook of Surgery, 14$^{th}$ edition, ed Sabiston, P.C. (W.B. Saunders, Philadelphia), pp. 510–550.
Ricketts, D., Turnbull, L., Ryall, G., Bakhshi, R., Rawson, N.S.B., Gazet, J.C., Nolan, C., & Coombes, R.C. (1991) Cancer Res. 51, 1817–1822.
Pike, M.C., Krailo, M.D., Henderson, B.E., Casagrande, J.T., and Hoel, D.G. (1983) Nature 303, 767–770.
Henderson, B.E., Ross, R.K., Judd, H.L., Krailo, M.D., and Pike, M.C. (1985) Cancer 56, 1206–1208.
Davis, D.L., Bradlow, H.L., Wolff, M., Woodruff, T., Hoel, D.G., and Anton–Culver, H. (1993) Environ. Health Pesp. 101, 372–377.
Walter, P., Green, S., Greene, G., Krust, A., Bornert, J.–M., Jeltsch, J.–M, Staub, A., Jensen, E., Scrace, G., Waterfield, M., & Chambon, P. (1985) Proc. Natl. Acad. Sci USA, 82, 7889–7893.
Ponglikitmongkol, M., Green, S., & Chambon, P. (1988) EMBO J. 7, 3385–3388.
Kumar V., Green S., Stack G., Berry M., Jin J. R. & Chambon P. (1987) Cell 51, 941–951.
Tora, L., White, J., Brou, C., Tasset, D., Webster, N., Scheer, E. & Chambon, P. (1989) Cell 59, 477–478.
Danielian, P.S., White, R., Lees, J.A. & Parker, M.G. (1992) EMBO J. 11, 1025–1033.
Roodi, N., Bailey, L.R., Kao, W. –Y., Verrier, C.S., Yee, C.J., Dupont, W.d., & Parl, F.F. (1995) J. of Natl. Cancer Inst 87, 446–451.
Lees, J.A., Fawell, S.E., White, R. & Parker, M.G. (1990) Mol. Cell. Biol. 10, 5529–5533.
Pfeffer, U., Fecarotta, E., Castagnetta, L., & Vidali, G. (1993) Cancer Res. 53, 741–743.
Zhang, Q. –X., Borg, A., & Fuqua, S.A.W. (1993) Cancer Res. 53, 5882–5884.
Castles, C.G., Fuqua, S.A.W., Klotz, D.M. & Hill, S.M. (1993) Cancer Res. 53, 5934–5939.
Miksicek, R.J. (1994) Cancer Biology 5, 369–379.

(List continued on next page.)

*Primary Examiner*—Michael G. Wityshyn
*Assistant Examiner*—Janet M. Kerr
*Attorney, Agent, or Firm*—Reising, Ethington, Barnes, Kisselle, Learman & McCulloch, P.C.

[57] ABSTRACT

A method is described for culturing morphologically and antigenically distinguishable types of normal human breast epithelial cells (HBEC) derived from reduction mammoplasty. Type I HBEC showed luminal and stem cell characteristics i.e. the ability to form budding/ductal structures when cultured on MATRIGEL and expressed a variant ER (~48 Kd) which has a deletion in the DNA binding domain (exon 2). In contrast, Type II HBEC with basal epithelial phenotype are ER-negative when cultured on MATRIGEL. Simian virus 40 (SV40) transformed Type I and Type II HBEC lines also expressed the variant ER. Tumors formed in athymic nude mice by in vitro transformed tumorigenic Type I cell lines, however, expressed a high level of wild type ER which was undetectable in these cells grown in vitro before and after tumor formation. Thus, there appears to be a differential ER mRNA splicing between the in vitro and in vivo milieu.

1 Claim, 9 Drawing Sheets

OTHER PUBLICATIONS

Pfeffer, U., Fecarotta, E., & Vidali, G. (1995) Cancer Res. 55, 2158–2165.

Fuqua, S.A. W. & Wolf, D.M. (1995) Breast Cancer Res. and Treat., 35: 233–241.

Rea, D. & Parker, M.G. (1996) Cancer Res. 56: 1556–1563.

Fuqua, S.A.W., Fitzgerald, S.D., Chamness, G.C., Tandon, A.K., McDonnell, D.P., Nawaz, Z., O'Malley, B.W., & McGuire, W.L. (1991) Cancer Res 51, 105–109.

Daffada, A.A. I., Johnston, S.R.D., Smith, I.E., Detre, S., King, N., & Dowsett, M. (1995) Cancer Res. 55, 288–293.

Petersen, O.W., Hoyer, P.E., & van Deurs, B. (1987) Cancer Res 47, 5748–5751.

Hammond, S.L., Ham, R.G. & Stampfer, M.R. (1984) Proc. Natl. Acad. Sci. USA 81, 5435–5439.

Band, V. & Sager, R. (1989) Proc. Natl. Acad. Sci USA 86, 1249–1253.

Kao, C.-Y., Namota, K., Oakley, c.S., Welsch, C.W., & Chang, C.-C. (1995) Carcinogenesis 16, 531–538.

Chang, C.-C, Liu, C.J., Deocampo, N., Kang, K.-S., & Trosko, J.E. (1996) Proceedings of the American Association for Cancer Research 37, 38.

Kang K.-S., Wilson, M.R., Hayashi, T., Chang, C.-C. and Trosko, J.E. (1996) Environ. Health Pespect. 104, 192–200.

Nomata, K., Kang, K.-S., Hayashi, T., Matesic, D.F., Lockwood, B., Chang, C.-C., Trosko, J.E. (1996) Cell Biology and Toxicology 12, 69–78.

Ferguson, A.T., Lapidus, R.G., Baylin, S.B. & Davison, N.E. (1995) Cancer Res 55, 2279–2283.

Weigel, R.J., Crooks, D.L., Iglehart, D., & deConinck, E.C. (1995) Cell Growth & Differentiation 6, 707–711.

Liu, H., Wormkem M., Safe, S.H., & Bjeldanes L.F. (1994) J. Natl. Cancer Inst. 86, 1758–1765.

Johnston, S.R.D., Saccani–Jotti, G., Smith, I.E., Salter, J., Newby, J., Coppen, M., Ebbs, S.R., & Dowsett, M. (1995) Cancer Res 55, 3331–3338.

Leygue, E.R., Watson, P.H., & Murphy, L.C. (1996) J. Natl. Cancer Inst. 88, 284–296.

Wang, Y., and Miksicek, R.J. (1991) Mol. Endocrinol 5, 1707–1715.

Fuqua, S.A.W., Fizgerald, S.D., Allred, D.C., Elledge, R.M., Nawaz, Z., McDonnel, D.P., O'Malley, B.W., Greene, G.L. & McGuire, W.L. (1992) Cancer Res., 52, 483–486.

Pfeffer, U., Fecarotta, E., Castagnetta, L., and Vidali, G. (1993) Cancer Res. 53, 741–743.

Fuqua, S.A.W., Alfred, D.C., Elledge, R.M., Elledge, R.M., Krieg, S.L., Benedix, M.G., Nawaz, Z., O'Malley, B.W., Greene, G.L. & McGuire, W.L. (1993) Breast Cancer Res. Treat. 26, 191–202.

Miksicek, R.J., Lei, Y., & Wang, Y. (1993) Breast Cancer Res. Treat 26, 163–174.

Ray, A., Prefontaine, K.E. & Ray, P. (1994) JBC 269, 12940–12946.

Seol, W., Choi, H–S., Moore D.D. (1996) Science 272, 1336–1339.

Potter, V.R. (1978) Br. J. Cancer 38, 1–23.

Petersen, O.W., Ronnov–Jessen, L., Howlett, A.R., and Bissell, M.J. (1992). Proc. Natl. Acad. Sci. USA 89; 9064–9068.

Yang, N.N., Venugopalan, M., Hardikar, S. and Glasebrook, A. (1996) Science 273, 1222–1225.

EXPRESSION OF ESTROGEN RECEPTORS IN TYPE I AND TYPE II HUMAN BREAST EPITHELIAL CELLS

This application is a continuation-in-part of U.S. application Ser. No. 08/558,786, Filed Nov. 16, 1995, now U.S. Pat. No. 5,814,511 which is a divisional of U.S. application Ser. No. 08/308,118, Filed Sep. 16, 1994, now U.S. Pat. No. 5,650,317, hereby incorporated by reference.

TECHNICAL FIELD

The invention is directed toward epithelial cells and in particular, human breast epithelial cells having stem cell characteristics.

BACKGROUND OF THE INVENTION

The estrogen receptor (ER) is a ligand-inducible transcription factor which regulates the expression of a variety of genes including some growth factors, hormones and oncogenes important for the growth of breast cancer (1, 2). Expression of the ER plays an important role in the pathogenesis and maintenance of breast cancer. In breast cancer patients, about two-thirds of tumors are ER-positive (3); 50% of these ER-positive tumors are estrogen-dependent and respond to endocrine therapy (4,5). Breast carcinomas occurring in postmenopausal women are often ER-positive (6), and many of these tumors express significantly more ER than does the normal mammary epithelium (7).

On the other hand, it has been proposed that the cumulative exposure of breast tissue to hormones associated with ovarian activity is a major determinant of breast cancer risk (8, 9). Furthermore, some environmental agents and dietary components might influence breast cancer development by functioning as xenoestrogens or estrogenic potentiating factors (10).

The ER gene spans 140 kb and is comprised of 8 exons which are spliced to yield a 6.3 kb mRNA, encoding a 595-amino acid protein with a molecular weight of 66 kilodaltons (11, 12). The ER protein is comprised of several discrete functional domains (13). Two transcriptional activation functions (TAF-1 and TAF-2) reside in exon 1 and 8 respectively (14–15). The DNA-binding domain of about 70 amino acids is located at exon 2 and 3. Exon 4 through 8 translating into 250 amino acids in size are necessary and sufficient for ligand binding (13, 16). A 22 amino acid sequence necessary for subunit dimerization has been located in exon 7 (17).

Recently, it has been reported that both the wild type and variant estrogen receptors were coexpressed in some human breast carcinoma cell lines (18–24). Variant human breast tumor ER with constitutive transcriptioanl activity has been identified in tumor specimens (25 & 26). Therefore, estrogen receptor variants might have a role in human breast cancer. However, to date, the role of the estrogen receptor variant in carcinogenesis and the regulation of its expression are poorly understood.

The human mammary gland contains a small but distinct population of ER-positive cells, comprising about 7% of the total epithelial cell population from all biopsies (27). The ER-positive cells were distributed as scattered single cells, most of them (87%) were luminal epithelial cells or occupied an intermediate position in the duct wall. The highest frequency of ER-positive cells has been found in the lobules as compared to the interlobular ducts (27). Normal HBEC grown in the commonly used media, MCDB 170 (28) and DFCI-1 (29), including the commercially available normal HBEC (Clonetics), exhibited basal epithelial, but not luminal epithelial cell characteristics. These cells have not been shown to express the estrogen receptor with significant frequency.

Recently, we have developed a culture method to grow two morphologically and antigenically distinguishable normal human breast epithelial cell (HBEC) types from reduction mammoplasty (30). Type I HBEC is deficient in gap junctional intercellular communication (GJIC) and has luminal and stem cell characteristics, i.e. the differentiation of Type I into Type II HBEC by a cyclic AMP-inducing agent (30) and the unique ability of Type I HBEC to form budding and ductal structures on MATRIGEL matrix (31), whereas Type II HBEC is capable of GJIC (30, 32–33) and expresses basal epithelial cell phenotypes (30). See U.S. ser. No. 08/308,118 filed Sep. 16, 1994 now U.S. Pat. No. 5,650,317, incorporated herein by reference.

It is an object of the present invention to describe a substantially purified human breast epithelial cell type (such as Type I HBEC) which has stem cell characteristics and which expresses human estrogen receptor.

It is also an object of the present invention to describe the expression of estrogen receptors in these two types of human breast epithelial cell (HBEC) and the neoplastically transformed cell lines derived from these cells.

SUMMARY OF THE INVENTION

A substantially purified epithelial cell comprised of characteristics of a stem cell and expressing human estrogen receptor.

BRIEF DESCRIPTION OF THE DRAWINGS

Other advantages of the present invention will be readily appreciated as the same becomes better understood by reference to the following detailed description when considered in connection with the accompanying drawings wherein:

FIG. 1. Western blot analysis for the expression of estrogen receptor, p53, bcl-2, p21, p16, and cyclin D1 expression. Panel A, same amount of protein from normal Type I (N) and SV40-transformed Type I HBEC at different stages of transformation (extended lifespan, E, immortal, I and tumorigenic, T) blotted on the same membrane were probed for the expression of cell cycle-related proteins and ER; Panel B, same as panel A, except normal Type II and SV40-transformed Type II HBEC and the control MCF-7 and T47D cells were used. In both experiments, the Ab-1 (Oncogene Science) anti-ER antibody which recognizes the C-terminal domain of ER was used; Panel C, the expression of ER in normal and SV40-transformed Type I and Type II HBEC was studied using the NCL-ER-LH2 (Vector lab.) anti-ER antibody which recognizes the N-terminal domain of ER. The cells used are HME-12, 14, 15 (lanes 1–3), HME-12, 14, 15 (lanes 4–6), M13SV1 (lane 7), M15SV1 (lane 8), M13SV22 (lane 9), M15SV26 (lane 10), M15SV29 (lane 11).

Panel A, Type I and SV40-transformed HBEC lines: lane 1–4 (HME-5, HME-12, HME-14, HME-15, repectively), lane 5–19 (M11SV1, M11SV2, M13SV1, M13SV2, M15SV1-11, respectively); Panel B, normal Type II and SV40-transformed Type II HBEC lines: lane 1–4 (HME-5, HME-12, HME-14, HME-15, repectively), lane 5–15 (M13SV22, M15SV21-30, respectively). The control RT-PCR for GAPDH are also shown.

FIG. 5. Electrophoretic Mobility Shift Assay (EMSA). Panel A, ER-ERE binding: free probe only (lane 1), and nuclear extracts from normal Type I HBEC (lane 2, HME-15) and normal Type II HBEC (lane 3, HME-15), SV40-transformed Type I HBEC (lane 4 and 5, M13SV1 and M15SV6, respectively), SV40 transformed Type II HBEC (lane 6, M13SV22) and MCF-7 (as a positive control, lane 7); Panel B, The specificity of the retarded bands was confirmed by the addition of an excess of unlabeled double-stranded olignucleotide. The retarded band was supershifted dramatically when the nuclear extract was preincubated with anti-ER antibody (Ab-1, Oncogene Science) before binding to ERE probe (lane 3), lane 1, free probe; lane 2, MCF-7 without anti-ER antibody; lane 4, MCF-7 with preimmune serum from mouse; lane 5, unlabeled oligonucleotide of ERE.

DETAILED DESCRIPTION OF THE INVENTION

The subject stem cell compositions may find use in a variety of ways. Since the cells are primitive and undifferentiated, they can be used to fully reconstitute an irradiated host and/or a host subject to chemotherapy; or used as a source of cells for specific lineages, by providing for their maturation, proliferation and differentiation into one or more selected lineages by employing a variety of factors, such as erythropoietin, colony stimulating factors, e.g., GM-CSF, G-CSF, or M-CSF, interleukins, e.g., IL-1, -2, -3, -4, -5, -6, -7, -8, etc., or the like, or stromal cells associated with the stem cells.

The stem cells may also be used in the isolation and evaluation of factors associated with the differentiation and maturation of hematopoietic cells. Thus, the stem cells may be used in assays to determine the activity of media, such as conditioned media, evaluate fluids for cell growth activity, involvement with dedication of particular lineages, or the like.

The stem cells may be used for the treatment of genetic diseases. Genetic diseases associated with hematopoietic cells may be treated by genetic modification of autologous or allogeneic stem cells to correct the genetic defect. For example, diseases such as B-thalas-semia, sickel cell anemia, adenosine deaminase deficiency, recombinase deficiency, recombinase regulatory gene deficiency, etc. may be corrected by introduction of a wild-type gene into the stem cells, either by homologous or random recombination. Other indications of gene therapy are introduction of drug resistance genes to enable normal stem cells to have an advantage and be subject to selective pressure, e.g. the multiple drug resistance gene (MDR). Diseases other than those associated with hematopoietic cells may also be treated, where the disease is related to the lack of a particular secreted product such as a hormone, enzyme, interferon, factor, or the like. By employing an appropriate regulatory initiation region, inducible production of the deficient protein may be achieved, so that production of the protein will parallel natural production, even though production will be in a different cell type from the cell type that normally produces such protein. It is also possible to insert a ribozyme, antisense or other message to inhibit particular gene products or susceptibility to diseases, particularly hematolymphotropic diseases.

The epithelial cells of the Type I that are obtained herein are stem cell in nature. Stem cells have utility for skin grafting techniques as well as for liver regeneration. They have utility for treating those that are suffering from anemia, Hodgkin's disease, or juvenile leukemia.

Being able to obtain the putative human breast epithelial stem cells of the present invention enables one to further perform research on carcinogenesis to develop chemopreventive and therapeutic strategies for breast cancer.

It is to be appreciated with the presence of the estrogen receptor as described herein in HBEC, one may readily test different compounds for their effectiveness to inhibit the activity of the estrogen receptor or to engage the estrogen receptor thereby inactivating it.

This study discovered a differential alternative splicing of human estrogen receptor (ER) under in vitro and in vivo conditions. The results suggest a new strategy to control the growth of estrogen-dependent human breast tumors, i.e. the modulation of the tissue environment in order to facilitate the alternative splicing that results in the expression of non-functional ER. This discovery, in brief, could provide a new strategy for cancer chemotherapy for tumors to render them estrogen-non-responsive.

It is also to be appreciated that with the knowledge of the estrogen receptor described herein, a cell can be transformed with a DNA sequence of the estrogen receptor, the DNA sequence being arranged in operative association with an expression control sequence capable of directing replication and expression of the DNA sequence.

The cells which are transformed can be mammalian or bacteria cells.

This case is also concerned with a method of identifying antagonists to the estrogen receptor comprising:
(1) providing a substantially purified epithelial cell comprised of stem cell characteristics and expressing estrogen receptor;
(2) culturing the cell line in a culture medium, whereby the receptor is expressed stably;
(3) adding an effective amount of an organic compound to said culture medium, sufficient to bind the compound to the receptor; and
(4) detecting the binding ability of the compound.

After the appropriate testing to determine antagonists is completed, one can then use the results for preparation of pharmaceutical compositions.

Therefore, the case is also directed to a pharmaceutical composition useful in the treatment of disease characterized by binding to the estrogen receptor in an epithelial cell comprising treating the cell with a therapeutically effective amount of the estrogen receptor antagonist in a pharmaceutically acceptable vehicle.

Materials and Methods

Cells and Cell Culture. Normal human breast epithelial cells were isolated from reduction mammoplasty of 4 different women (21–29 years of age, designated HME-5, 12, 14, 15). The media and the procedure used to develop the two types of normal HBEC have been described previously (30). The primary cultures developed in vitro for one week were stored in liquid nitrogen. Early passage cells, after recovery from liquid nitrogen storage, were used in these experiments. All cell cultures were grown at 37° C. in incubators supplied with 5% $CO_2$ and humidified air.

Transformation of normal HBEC was achieved by lipofectin-mediated transfection of HBEC (30) with SV40 DNA (GIBCO-BRL) (M11SV2, M13SV1, M13SV22 derived from normal HBEC cultures HME-11 and HME-13 respectively) or a plasmid carrying the G418-resistance gene and an origin-defective SV40 genome expressing a wild type large T-antigen (pRNS-1 obtained from Johng S. Rhim of the National Cancer Institute) (M15SV1-11, M15SV21-29 derived from HME-15). In addition to the ER-positive MCF-7, T47D and the ER-negative MDA-MB-231 breast cancer cell lines, a HBEC line (M12 B4 derived from HME-12), with extended lifespan after 5-bromodeoxyuridine treatment, was also included in the study of ER expression.

Immune fluorescence Staining of Estrogen Receptor. Cells were fixed by 4% paraformaldehyde for 20 min., postfixed with absolute methanol for 30 sec and then rehydrated with phosphate buffered saline (PBS). Subsequently, nonspecific binding sites were blocked with 10% normal goat serum (NGS) in PBS for 30 min at room temperature. The cells were incubated overnight at 4° C. with a primary antibody against ER (Ab-1, Oncogene Science, NY; diluted 1: 200 in PBS containing 0.1% BSA and 1% NGS), washed three times with PBS, and then incubated with a second anti-mouse antibody conjugated with rhodamine (Jackson Immunoresearch Lab, West Grove, Pa.; diluted 1:100 in PBS) for 30 min at room temperature. The cells were washed extensively with PBS containing 0.1% BSA and 1% NGS and mounted with coverslips on Poly-aquamount (Polysciences, Inc., Warrington, Pa.). The cells were examined and photographed using the Ultima laser confocal scanning microscope (Meridian Instruments, Okemos, Mich.).

SDS-PAGE and Western Blot Analysis. Proteins were extracted from normal and SV40-transformed HBEC, and from MCF-7, T47D, MDA-MB-231 cells in 100 mm dishes by treatment with 20% SDS lysis solution containing several protease and phosphatase inhibitors (1 mM phenylmethylsulfonyl fluoride, 1 uM leupeptin, 1 uM antipain, 0.1 uM aprotinin, 0.1 uM sodium orthovanadate, 5 mM sodium fluoride). After sonication at three 10-sec pulses from a probe sonicator, the cell lysates were stored at −20° C. until use (32). The protein amounts were determined by the DC protein assay kit (Bio-Rad Co., Richmond, Calif.). Proteins were separated on 12.5% SDS polyacrylamide gels and transferred to PVDF membranes at 20 V for 16 hr. ER was detected by the anti-ER monoclonal antibody (NCL-ER-LH2, Vector Lab., Burlingame, Calif.) which recognizes the amino (N)-terminal portion of ER and by the anti-ER monoclonal antibody (Ab-1, oncogene science, NY) which recognizes the carboxyl (C)-terminal portion of ER after blocking with 5% dried skim milk in PBS containing 0.1% Tween 20. This was then followed by incubation with horseradish peroxidase-conjugated secondary antibody and detected with the ECL chemiluminiscent detection reagent (Amersham Co., Arlington Heights, Ill.). The membranes were exposed to X-ray film for 15 sec to 1 min.

Reverse Transcription-Polymerase Chain Reaction (RT-PCR). Total RNA was extracted from cells by using Trizol reagent (GIBCO-BRL, Gaithersburg, Md.) according to the manufacturer's protocol. The extracted RNA was dissolved in RNase-free water, and its concentration and purity was determined by a spectrophotometer.

cDNA was synthesized from the isolated RNA by reverse transcription in 20 ul reaction solution containing 2.5 uM of random hexamers (Perkin Elmer, Madison, Wis.), 50 units of Moloney murine leukemia virus reverse transcriptase (Perkin Elmer, Madison, Wis.), 1 ug of total RNA, 2 ul of 10×PCR buffer (500 mM KCl, 100 mM Tris-HCl, pH 8.3), 5 mM $MgCl_2$, 1 mM of each dNTP, 20 units of RNase inhibitor (Perkin Elmer, Madison, Wis.), and 2 ul of RNase free water (Promega, Madison, Wis.). The reaction mixture was incubated at room temperature for 10 min and then at 42° C. for 15 min, heated to 99° C. for 5 min, and then quick-chilled on ice. The 20 ul of solution which contains the reverse transcribed cDNA were added to 30 ul of PCR reaction mixture containing 2 mM $MgCl_2$, 3 ul of 10×PCR buffer, 25 pmol of each primer and 1.25 units of AmpliTaq DNApolymerase (Perkin Elmer, Madison, Wis.). The primers chosen for PCR are sequences surrounding the border between exon 7 and 8 of the ER (5'-GCACCCTGAAGTCTCTGGAA-3' Seq. ID No: 1, 5'-TGGCTAAAGTGGTGCATGAT-3' Seq. ID No: 2) (34) and sequences encompassing exon 2 of the ER (5'-TACTGCATCAGATCCAAGGG-3' Seq. ID No: 3, 5'-ATCAATGGTGCACTGGTTGG-3' Seq. ID No: 4) (35). The primers used to generate the 306-bp GAPDH products were 5'-CGGAGTCAACGGATTTGGTCGTAT-3' Seq. ID No: 5 and 5'-AGCCTTCTCCATGGTGGTGAAGAC-3' Seq. ID No: 6. Thermal cycling was performed in a Gene-AMP 9600 PCR system (Perkin Elmer, Madison, Wis.) by using the following 2 steps amplification profile: an initial denaturation at 95° C. for 105 sec, 35 cycles of denaturation at 95° C. for 15 sec, and annealing at 60° C. for 30 sec; and a final elongation step at 72° C. for 7 min. The PCR products were then electrophoresed in a 2% agarose gel and stained with 0.5 ug/ml ethidium bromide. The size of cDNA product was determined by comparison to DNA size markers (the HaeIII digested X174 DNA, GIBCO-BRL, Gaithersburg, Md.).

ER-ERE Binding Assay. Nuclear extracts were prepared as previously described (36). Cells were lysed with hypotonic buffer (10 mM HEPES, 1.5 mM, $MgCl_2$, pH 7.5) and nuclei were pelleted by centrifugation at 3000 g for 5 min. Nuclear lysis was performed using a hypertonic buffer (30 mM HEPES, 1.5 mM $MgCl_2$, 450 mM Kcl, 0.3 mM EDTA, and 10% glycerol) with 1 mM DTT, 1 mM PMSF, and 1 ug/ml of aprotinin and leupeptin. Following lysis, the samples were centrifuged at 12,000 g for 30 min, and the supernatant was collected for use in the DNA binding assay. Double-stranded oligonucleotides, containing a wild-type estrogen responsive element (ERE) consensus sequence (5'-GTCCAAAGTCAGGTCAGTGACCTGATC AAAGTT-3') Seq. ID No: 7, that corresponds to -308/-342 of the promoter/upstream element of the Xenopus vitellogenin A2 gene (36), was synthesized at the Biotechnology facility of Michigan State University. The ERE was annealed, and end-labeled with [$\gamma$-$^{32}$P]. The nuclear extract (3 ug) was incubated with the reaction buffer [70 mM Kcl, 30 mM HEPES (pH 8.0), 1.5 mM $MgCl_2$, 0.3 mM EDTA, 10% glycerol, and 2 ug poly (dI-dC)] in the presence or absence of unlabeled oligonucleotide competitor, or antibody for 10 min, followed by a 20 min incubation at room temperature with the $^{32}$P-labelled ERE DNA probe. The products of ER and ERE DNA binding activity was separated from free probe in a 4.8% polyacrylamide gel by electrophoresis using TBE buffer (89 mM Tris, 89 mM boric acid, and 2 mM EDTA). After electrophoresis, the gel was dried and subjected to autoradiography.

Tumor Development in Athymic Nude Mice. Cells suspended in 0.25 ml of MSU-1 medium (30) with 5% FBS were injected subcutaneously into each of two sites on a female athymic nude mouse (Harlan-Sprague-Dawley). The tumors formed from 6×10$^6$ cells innoculated in each site were dissected and measured four weeks after innoculation. The tumor cells were removed for protein extraction for Western blot analysis and for reestablishment of cell cultures which were also harvested for Western blot analysis.

MSU-1 medium is described in applicant's U.S. Pat. No. 5,650,317 and is comprised of calcium chloride, sodium bicarbonate, sodium chloride, sodium phosphate, amino acids, glucose and sodium acetate.

Growth of Human Breast Epithelial Cells on Matrigel. The undiluted growth factor reduced MATRIGEL Matrix (Collaborative Biomedical Products, Becton Dickinson Labware) was used to prepare the basement membrane matrix. The separated pure Type I or Type II or a mixture of Type I and Type II HBEC in 2 ml of the defined MSU-1 medium was plated on top of the layer of the MATRIGEL Matrix (2.5 ml per 6 cm plate). The medium was renewed once every 3 days. The ductal and "budding" structures were formed 3 weeks after the cell plating.

RESULTS

Figure 1:
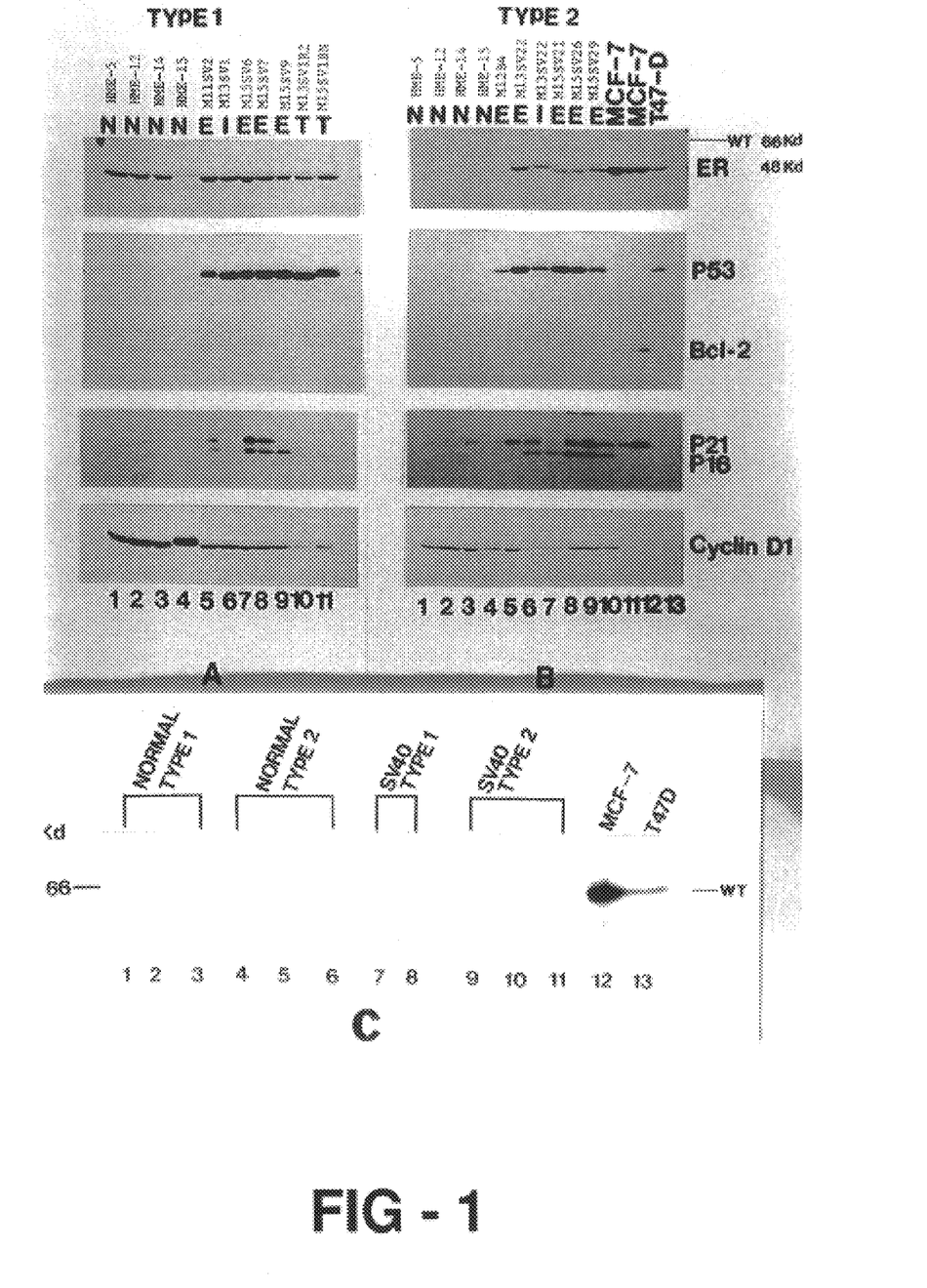

Expression of Estrogen Receptor in Normal HBEC. Type I and Type II normal HBEC derived from reduction mammoplasty of four different women (HME-5, 12, 14, 15) were examined for their ER expression by Western blot analysis using an anti-ER antibody which recognizes the C-terminal region of ER (Ab-1, Oncogene Science). The results show that all the four Type I HBEC expressed an ER, whereas all the four Type II HBEC did not express any ER (FIG. 1A and 1B). The ER expressed in Type I HBEC, however, is not the wild type ER since its molecular size (approximately 48 kd) is smaller than the wild type ER (~66 kd). This variant ER appears to contain a deletion in N-terminal region, based on the observation that, unlike the ER-positive MCF-7 and T47D cells which express both wild type and variant ER, the ER was not detectable in Type I or Type II HBEC when anti-ER antibodies which recognize the N-terminal region (NCL-ER-LH2, Vector Laboratory; C314, Santa Cruz) were used (FIG. 1C).

Figure 2:
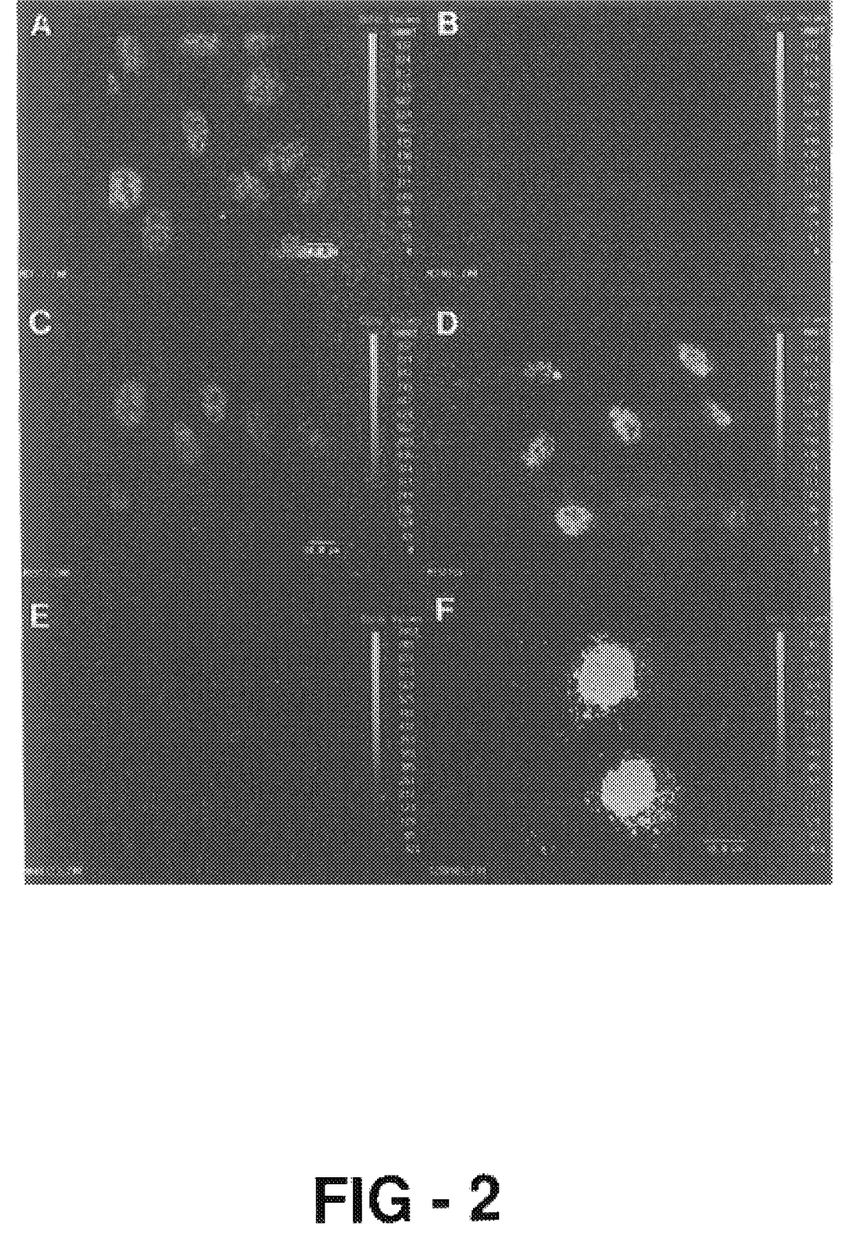
FIG. 2. Immunofluorescence staining for ER using the Ab-1 (Oncogene Science) anti-ER antibody. A and B, MCF-7 with and without primary antibody, respectively as controls; C and D, normal and SV40-transformed Type I HBEC (HME15 and M15SV1), repectively; E and F, normal and SV40-transformed Type II HBEC (HME15 and M15SV29), respectively.

The expression of ER in Type I, but not Type II normal HBEC was confirmed by immunofluorescence staining using Ab-1 anti-ER antibody (FIG. 2C and 2E). In this study, the ER was found to be expressed in all Type I HBEC colonies examined (more than 100) and in every cell in a colony (data not shown). Similar to Western blot analysis, the ER was detectable using the C-terminal anti-ER antibody (i.e., Ab-1) and not detectable using the N-terminal anti-ER antibodies (i.e. NCL-ER-LH2 and C314).

ER Expression in SV40-Transformed Type I and Type II HBEC. Similar to the Type I normal HBEC, SV40 transformed Type I HBEC lines (derived from three different primary cultures) at different stage of neoplastic transformation (extended lifespan, immortal, and tumorigenic) expressed the variant ER (~48 kd) (FIG. 1A) at similar expression levels as their parental cells, detected by Western blotting. Interestingly, unlike Type II normal HBEC, SV40 transformed Type II HBEC lines also expressed this variant ER (FIG. 1B). In contrast, a cell line with extended lifespan after 5-bromodeoxyuridine (BrdU) treatment (M12B4) did not express the ER (FIG. 1B). As expected, the ER of SV40-transformed Type I and Type II HBEC were found in the nuclei (FIGS. 2D & 2F) similar to MCF-7 cells (FIG. 2A) using the Ab-1 anti-ER antibody. However, we could not detect any ER in the SV40-transformed Type I and Type II HBEC, using antibodies which recognize the N-terminal region of the ER (NCL-ER-LH2, Vector lab; C314, Santa Cruz), by Western blot analysis (FIG. 1C) or by immunofluorescence staining (data not shown). In order to understand the function of this variant ER, we also examined progesterone receptor (PgR) expression which might be induced by estrogen in cell strains and cell lines studied in FIG. 1A and 1B. None of these cells were found to expressed the PgR (data not shown).

Figure 3:
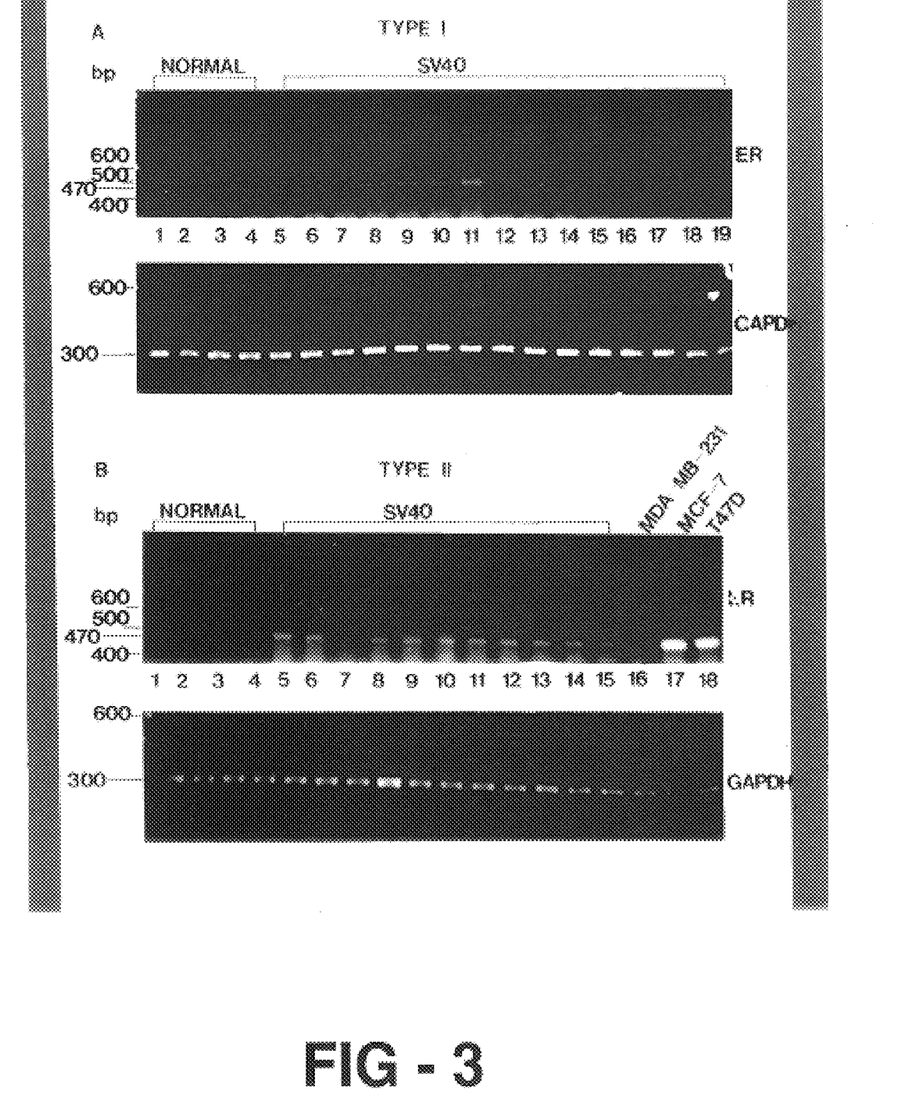
FIG. 3. RT-PCR analysis for detecting ER transcripts using primer pairs in the border between exon 7 and exon 8.
Figure 4:
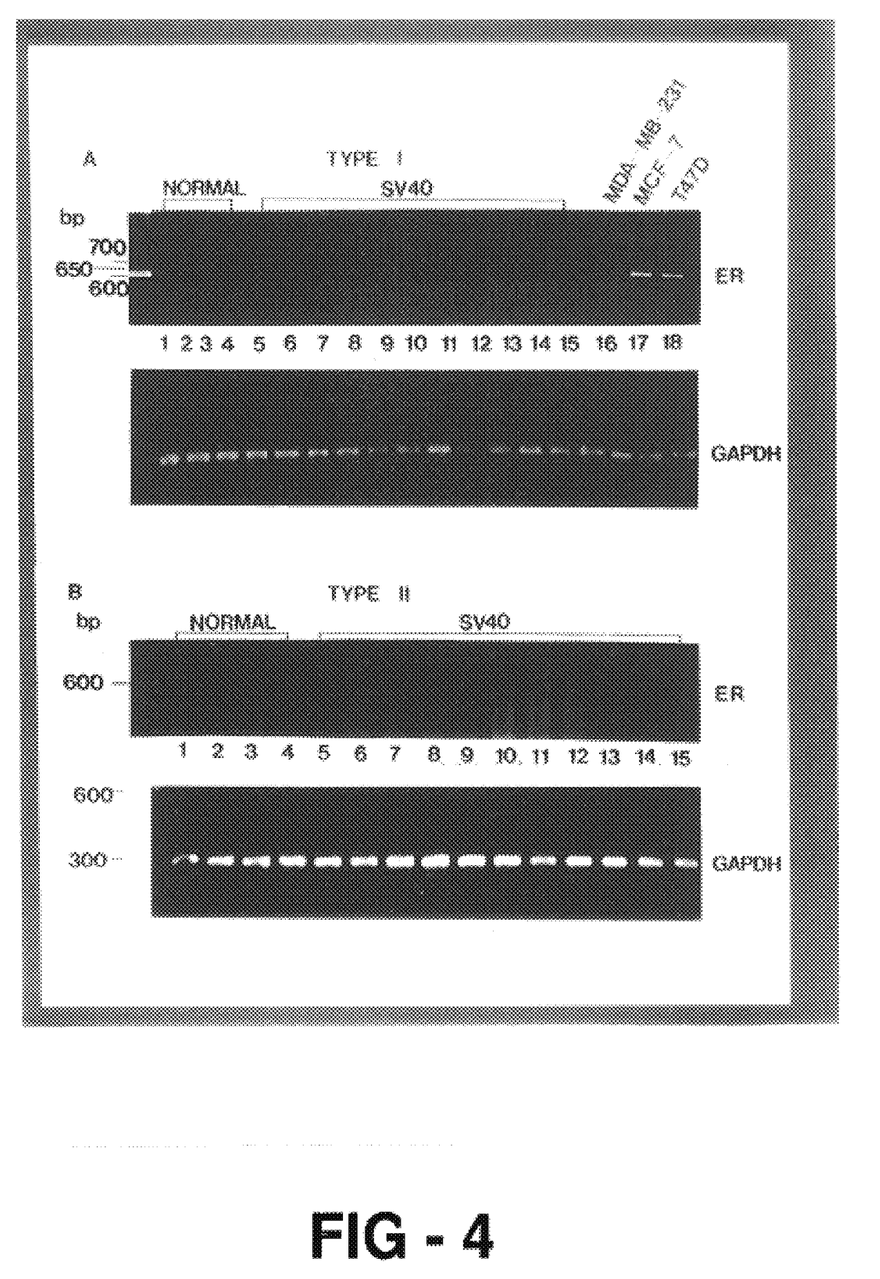
FIG. 4. RT-PCR analysis for detecting ER transcripts using primer pairs encompassing exon 2. Panel A, Type I and SV40-transformed HBEC lines: lane 1–4 (HME-5, HME-12, HME-14, HME-15, repectively), lane 5–16 (M11SV1, M13SV1, M15SV1-10, respectively); Panel B, normal Type II and SV40-transformed Type II HBEC lines: lane 1–4 (HME-5, HME-12, HME-14, HME-15, repectively), lane 5–15 (M13SV22, M15SV21-30, respectively). The control RT-PCR for GAPDH are also shown.

ER Expression by RT-PCR Analysis. To verify the above results and to gain more insight into the nature of the expressed variant ER, RT-PCR was performed using primer pairs encompassing exon 2 or a contiguous region bordering exons 7 and 8. As controls, RNA from the ER-positive MCF-7, T47D and the ER-negative MDA-MB-231 breast cancer cell lines were reverse transcribed, and then the cDNAs were amplified by PCR in conjunction with studies using Type I and Type II normal HBEC, as well as SV40-transformed Type I and Type II HBEC. As shown in FIG. 3, when primer pairs surrounding a region bordering exon 7 and exon 8 of the ER were used for PCR, a ~470 base pair product was detected in Type I but not in Type II normal HBEC or in the ER negative MDA-MB-231 cells. The amplified DNA was also found in SV40 transformed Type I and Type II HBEC, as well as in the ER-positive MCF-7 and T47D cells. The RT-PCR condition appears similar for all the cell strains or cell lines tested as judged from the uniform control amplification for the GAPDH gene. When primer pairs encompassing the exon 2 of ER were used for the PCR, none of the normal or SV40 transformed Type I or Type II HBEC yielded the ~650 base pair product as did the ER-positive MCF-7 and T47D cells (FIG. 4). These results confirm previous results that showed a variant ER was expressed in normal Type I HBEC and both Type I and Type II SV40 transformed HBEC. In addition, the study further indicates that the variant ER contains a deletion in the exon 2 region of the ER.

Figure 5:
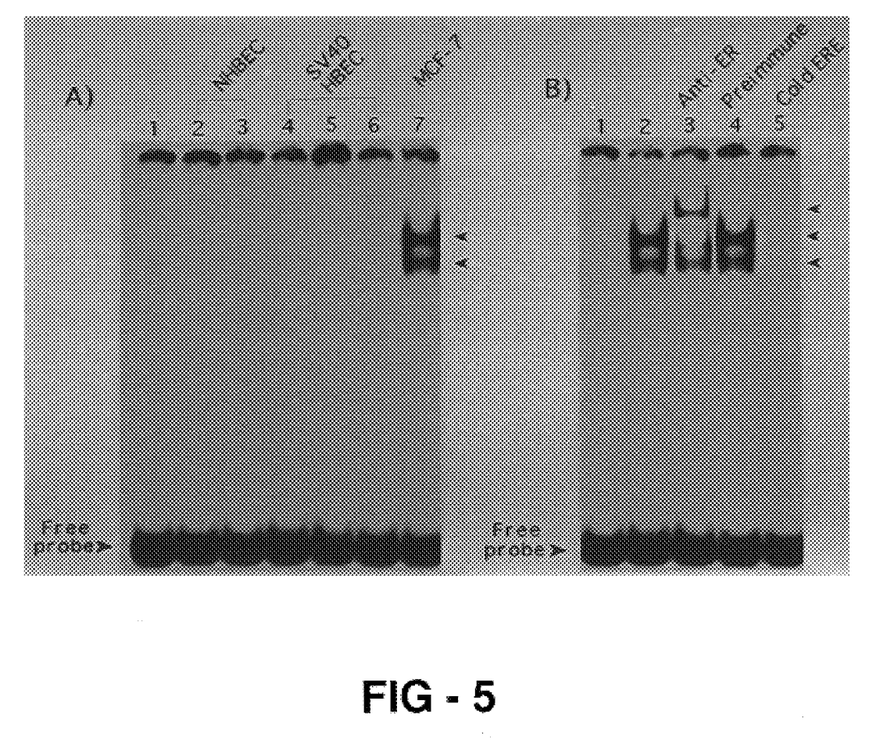

The Ability of the Variant ER to Bind an Estrogen Responsive Element. If the expressed variant ER contains a deletion in the DNA binding domain (exon 2), this ER is expected to lose its ERE DNA binding ability. To test if this is the case, nuclear extracts were prepared from cell lines expressing the variant ER and then subjected to a ER-ERE binding assay using a ERE motif, the cognate binding site for estrogen receptor. The results showed that the variant ER expressed in normal and SV40 transformed cells was deficient in ERE binding activity, while MCF-7 cells, as a positive control, produced a strong binding signal (FIG. 5A). The specificity of the retarded ER-ERE band observed for MCF-7 cells was confirmed by the addition of an excess of unlabeled double-stranded oligonucleotide. As shown in FIG. 5B, the retarded band was supershifted when the nuclear extract was preincubated with anti-ER antibody (Ab-1) before its binding to the ERE probe (FIG. 5B). These results are consistent with previous RT-PCR and Western blot analyses and clearly indicate that this variant ER had a deleted DNA binding region.

Figure 6:
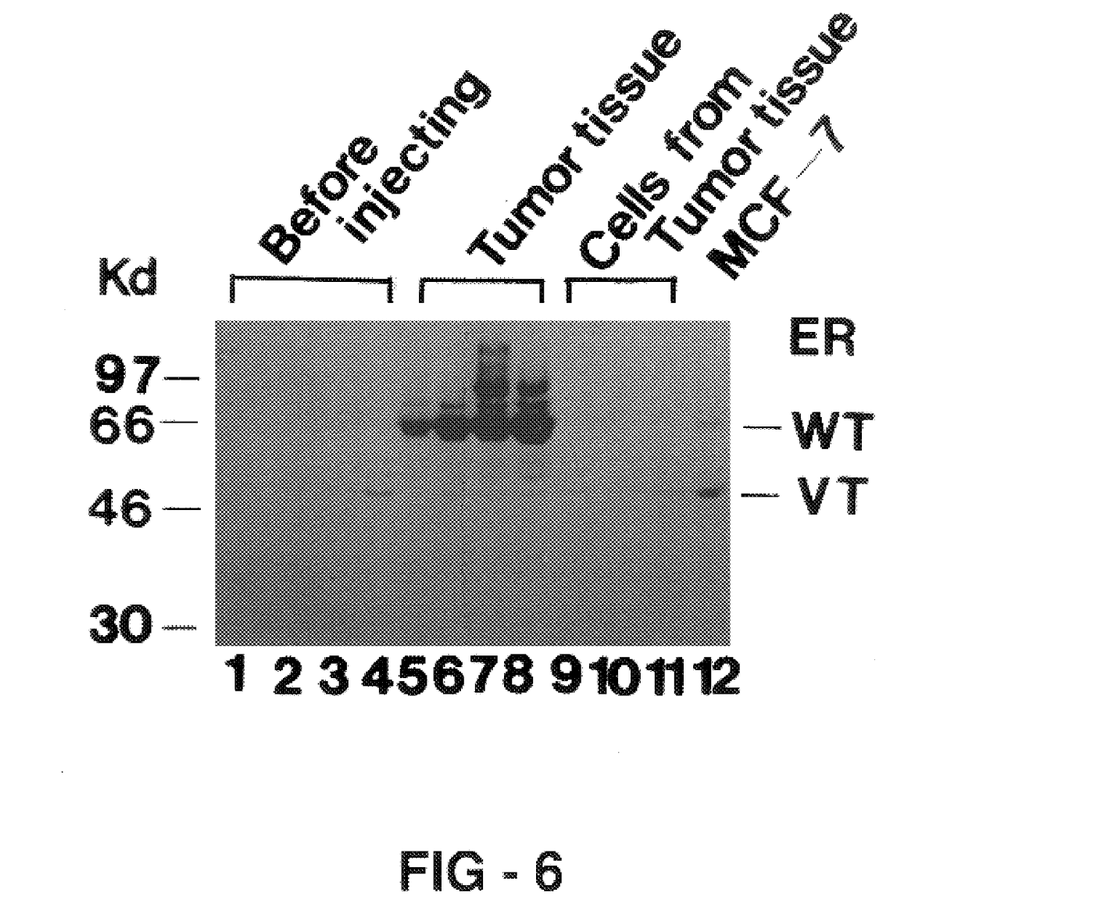
FIG. 6. Western blot analysis for the expression of ER. The expression of ER in weakly tumorigenic cell line, M13SV1R2 and highly tumorigenic cell lines, M13SV1R2-N1, -N4, -N8, before inoculation for tumor growth in nude mice (lane 1–4) and after reestablishment of cell culture from tumors (lane 9–11), were compared with that in tumors formed by these cells (lane 5–8). The cell lysates loaded are; lane 1, 5, 9, M13SV1R2; lane 2, 6, 10, M13SV1R2-N1; lane 3, 7, 11, M13SV1R2-N4; lane 4, 8 M13SV1R2-N8. The positions of wild type ER (WT) and Variant ER (VT) are indicated.
Figure 7:
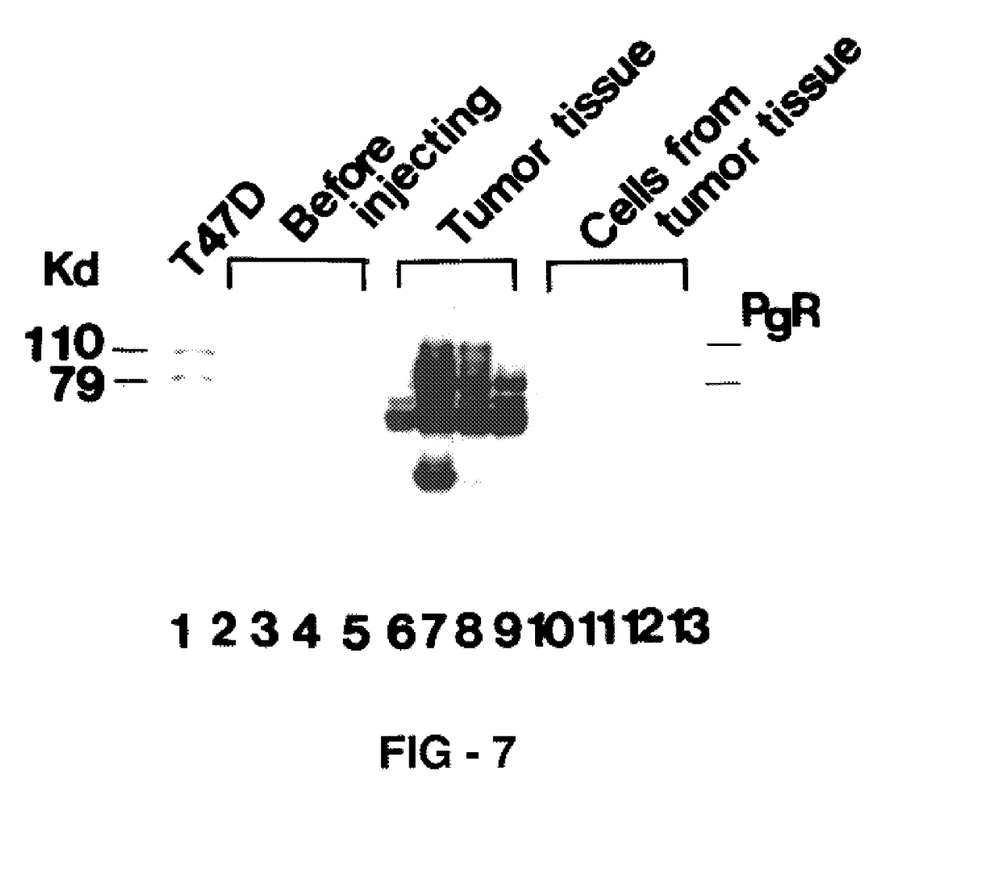
FIG. 7. The proteins from cell lines used in experiments presented in FIG. 6 also were used for Western blot analysis for the expression of PgR. The PgR expression in these cells before inoculation for tumor growth in nude mice (lane 2–5) and after reestablishment of cell culture from tumors (lane 10–12) were compared with that in tumors formed by these cells (lane 6–9). The cell lysate loaded are: lane 2, 6, 10, M13SV1R2; lane 3, 7, 11, M13SV1R2-N1; lane 4, 8, 12, M13SV1R2-N4; lane 5, 9, 13 M13SV1R2-N8.

Expression of Wild Type and Variant ER in Tumors Formed in Nude Mice by Neoplastically Transformed Type I HBEC. The SV40 immortalized Type I HBEC line (M13SV1) reported previously (30) was non-tumorigenic. After X-ray irradiation (2 Gy, twice), large colonies formed in soft agar were found to be weakly tumorigenic in athymic nude mice (a cell line, M13SV1R2 used in this study). The weakly tumorigenic cells became highly tumorigenic (tumor>1 cm formed in 4 weeks) after infection with a viral vector carrying a mutated neu oncogene (i.e., M13SV1R2-N1, -N4, -N8) (manuscript in preparation). We have tested the expression of ER in these tumorigenic cell lines before inoculation in nude mice, in tumors formed by these cells in nude mice and in the cell culture reestablished from tumors. The results showed that cells, before injection into nude mice, and cells, reestablished from tumor tissue, in vitro, only expressed the variant ER (~48 kd) using an anti-ER antibody recognizing the C-terminal region of the ER (Ab-1, Oncogene Science). Significantly, the tumor tissues expressed a high level of the wild type ER (~66 kd) and less amount of the variant ER (~48 kd) by Western blotting using both Ab-1 (Oncogene Science) (FIG. 6) and the human ER specific antibody (D75, kindly provided by Dr. Geoffrey Greene of University of Chicago) (data not shown). Western blot analysis for the expression of progesterone receptor using an anti-PgR antibody (Ab-1, Oncogene Science) was also carried out in these cells. The results are similar to that observed for the expression of ER (i.e., expression was found in tumor tissues but not in cells grown in vitro) (FIG. 7), indicating that the wild type ER expressed in vivo might be functional.

Expression of Cell Cycle Related Proteins (p53, $p21^{waf}$, $p16^{INK4}$, cyclin $D_1$) The same Western blots studying ER expression (FIG. 1) were also probed for the expression of cell cycle related proteins. As expected, high levels of p53 were found in SV40 transformed cell lines, confirming the involvement of large T antigen in their transformation. The p21 and p16 proteins were frequently elevated in transformed Type I and Type II HBEC cells. The cyclin D1 was highly expressed in Type I normal HBEC compared to their Type II HBEC counterparts. The transformation by SV40 reduced the expression of Cyclin D1 in Type I but not Type II HBEC.

Figure 8A:
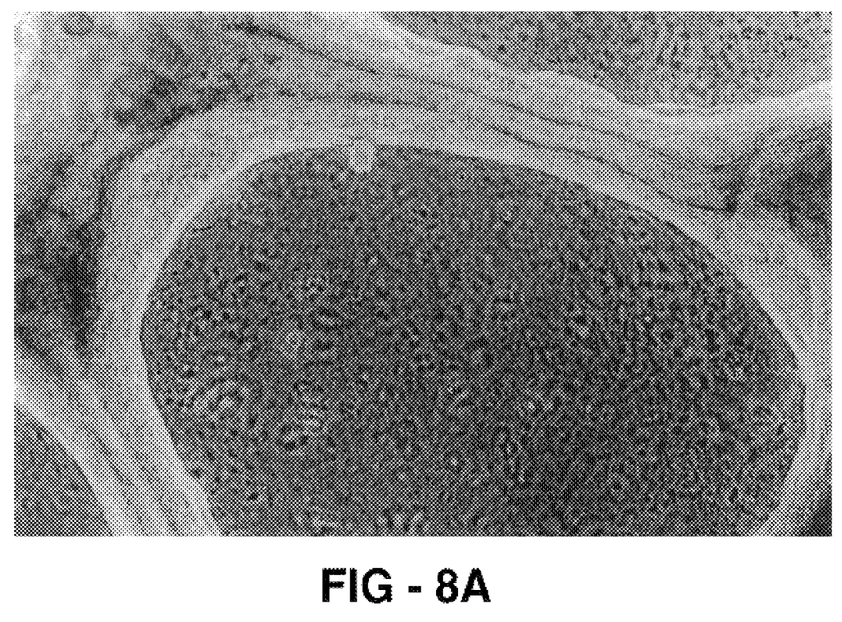
FIG. 8. Budding structures formed by Type I or a mixture of Type I and Type II HBEC (HME-15) on MATRIGEL in MSU-1 medium 19 days after cell inoculation.
Figure 8B:
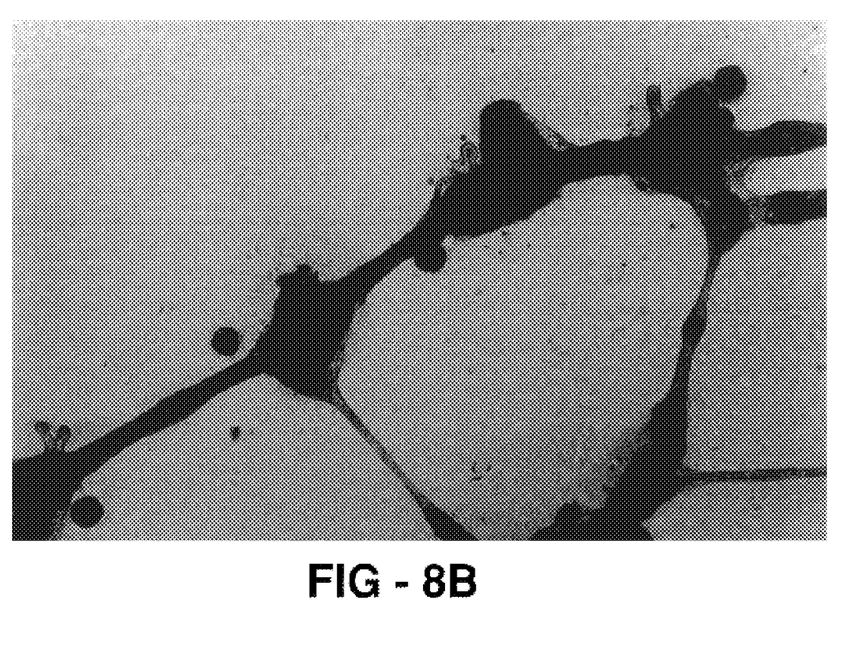
Figure 9A:
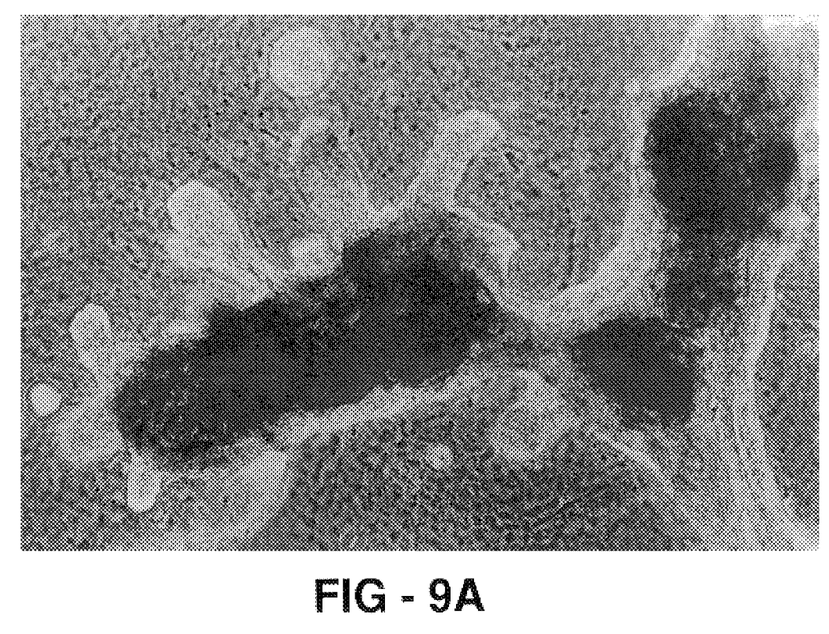
FIG. 9. "Ductal" structures formed by Type I (top) or a mixture of Type I and Type II HBEC (HME-15) (bottom) on MATRIGEL in MSU-1 medium 4 weeks after cell inoculation. Photos were taken at different magnification: (Top, ~90×, Bottom, ~36×) using a Nikon phase contrast microscope without staining.
Figure 9B:
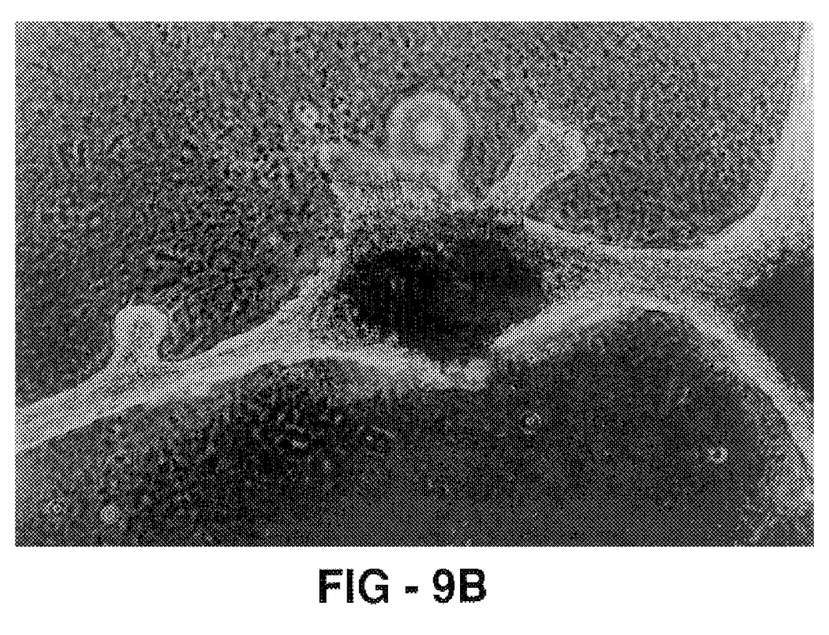

Unique Ability of Type I Human Breast Epithelial Cells To Form "Ductal" and Budding Structure on MATRIGEL. Petersen et al., (47) have reported that human breast epithelial cultures enriched for luminal epithelial cells were capable of forming multicellular spherical colonies (acini) on MATRIGEL. In this study, we found that our Type I HBEC also were capable of forming these small spheres on MATRIGEL. In addition, we also observed that Type I HBEC or a mixture of Type I and Type II HBEC was capable of forming "ductal" (FIG. 8) and terminal end bud-like (FIG. 9) structures on MATRIGEL. Type II HBEC alone lacked this ability, but were capable of forming large spheres which appear hollow inside (data not shown). Since terminal end buds are believed to contain stem cells, the unique ability of Type I HBEC to form these structures provides further evidence that Type I HBEC have stem cell characteristics.

The major finding of the above study is that an estrogen receptor was expressed in all the Type I HBEC with luminal and stem cell characteristics examined while their Type II HBEC counterparts with basal cell characteristics did not express any ER. Furthermore, all the SV40 transformed Type I and Type II HBEC lines examined (15 and 11 cell lines, respectively) were also found to express the ER. Although the human mammary gland is known to contain a small population of ER-positive cell (27), the previously reported normal HBEC in culture have not been shown to express the ER with significant frequency. The expression of ER in the Type I HBEC or SV40 transformed cells is unambiguous since it has been observed by three different methods (i.e., Western blot analysis, immunofluorescence staining, and RT-PCR).

The ER expressed, however, is not the wild type ER. It is a variant ER with smaller molecular weight (~48 kd) than the wild type ER (~66 kd). This variant ER was detectable by Western blot analysis and immunofluorecence staining using an anti-ER antibody (Ab-1, Oncogene Science) recognizing the C-terminal portion of the ER but was undetectable when anti-ER recognizing the N-terminal portion of the ER (NCL-ER-LH2, Vector laboratory, C314, Santa Cruz) were used. This observation suggests that the variant ER contains a deletion in the N-terminal region. By RT-PCR analysis using primer pairs in the C-terminal or N-terminal region, the deletion was found to be in the exon 2 region. Since exon 2 is a part of DNA binding domain, the ER with deletion in this region is expected to lose its DNA-binding activity. This was found to be true in the ER-ERE binding assay. That the variant ER deleting DNA binding domain would be non-functional is revealed by the non-expression of the PgR which is positively regulated by the ER (37). Recently, ER variants with deletion in exon 2, exon 3, or both were observed in normal human breast tissue (38).

Of the eight exons that constitute the ER mRNA transcript, most of them (exon 2–7) have been found to be involved in aberrant splicing events in breast tumor cell lines or tissues (39–43). Many of these variants disrupt critical regions such that they become non-functional (21). The variant ER expressed in our cells appears to belong to this category. Some other variants may play an important role in tumor growth, e.g., variant ER lacking the hormonal binding domain is suspected to be a dominant positive transcriptional activator that account for hormone independent growth of tumors (25, 26). Furthermore, variants ER lacking the DNA binding domain might function as negative transcription factors through a different mechanism (44, 45). Indeed, Yang et al. have recently shown that human tranforming growth factor-β3 gene can be activated by the estrogen receptor in the presence of estrogen metabolites or estrogen antagonists. Activation was mediated by a polypurine sequence, termed the raloxifene response element, and did not require the DNA binding domain of the estrogen receptor (48).

Although the ER expressed in Type I and SV40 transformed HBEC appears to be non-functional, there is evidence that this is only an in vitro phenomenon. From studies presented in FIG. 6 and FIG. 7, tumorigenic cell lines derived from Type I HBEC were found to express high level of wild type ER in tumors formed by these cells in athymic nude mice. The same cells did not express the wild type ER before inoculation for tumor growth or after the tumor cells were cultured in vitro. The wild type ER expressed in tumors have been shown to be human ER as they were observed by Western blot anaysis using a human ER specific antibody. The expressed wild type ER in tumors appears to be functional since the PgR was simultaneously expressed.

The expression of the variant ER in SV40 transformed Type II HBEC is unexpected. The mechanism for its expression is not clear. One possible mechanism is that the expression of large T-antigen induced the expression of ER. We have tested the hypothesis by transfecting the ER-negative MDA-MB-231 breast adenoma cells with SV40. The MDA-MB-231 cells expressing the large T-antigen resulted from SV40 transfection, however, remained ER-negative. Alternatively, in the Type II HBEC population, there might exist a small population of ER-positive transitional cells, newly differentiated from Type I cells, which were the target cells for SV40 transformation. Except for ER expression, the phenotypes of SV40 transformed Type II HBEC are substantially different from that of SV40 transformed Type I cells (30). Therefore, these hypothetical transitional cells are quite different from the Type I HBEC.

The implication of the above results is twofold. First, the expression of ER in Type I HBEC provides additional similarity between breast cancer cells and Type I HBEC. As mentioned previously, the origin of the ER-positive tumors is not known. One possible origin is that they were derived from ER-positive normal HBEC stem cells similar to our Type I HBEC. During the neoplastic transformation, many of the parental target cell phenotypes are largely preserved. Those include deficiency in gap junctional intercellular communication, expression of luminal epithelial cell markers (30), and expression of telomerase. Our study also indicates that Type I HBEC are more susceptible to neoplastic transformation by an oncogenic (SV40) stimulus (i.e., to become immortal and capable of anchorage independent growth) (30). The phenotypic similarity between Type I HBEC and breast cancer cells mentioned above are consistent with the notion of oncogeny as blocked or partially blocked ontogeny (46). Second, our results indicate that there is a differential splicing in ER mRNA under in vitro and in vivo conditions. The expression of a variant ER under our in vitro culture condition might be an indication that the same cells might express the wild type ER in vivo. Furthermore, the results suggest a potential strategy to control the growth of estrogen-dependent human breast tumors, i.e., the modulation of the tissue environment in order to facilitate the alternative splicing that results in the expression of non-functional ER. Lastly, this study raises an awareness concerning limitations in interpretation of experimental results. First, the use of immunostaining to classify tumors as ER-positive or ER-negative based on the use of one antibody may not be adequate. It may not detect all alternatively spliced ER nor provide the information concerning its function. Second, the phenotype of a normal cell type used for comparison with that of tumor cells may be irrelevant. For example, when we describe normal HBEC as proficient in gap junctional intercellular communication and ER-negative, they apply to Type II but not Type I HBEC. In other words, not all normal cells have the same phenotype in a given tissue. Thirdly, gene expression in vitro could be dramatically different from gene expression in vivo. This is exemplified by the wild type ER expression in Type I HBEC-derived tumorigenic cells as demonstrated in this study.

While the forms of the invention herein disclosed constitute presently preferred embodiments, many others are possible. It is not intended herein to mention all of the possible equivalent forms or ramifications of the invention. It is understood that the terms used herein are merely descriptive rather than limiting, and that various changes may be made without departing from the spirit or scope of the invention.

REFERENCES

1. Gronemeyer, H. (1991) *Ann. Rev. Genetics* 25, 89–123.
2. Dickson, R. B. & Lippman, M. E. (1994) in *The Molecular Basis of Cancer*, eds. Mendelsohn, J., Howley, P. M., Israel, M. A., & Liotta, L. A., (W. B. Saunders Co., Philadelphia), pp. 358–384.
3. Lippman, M. E., and Allegra, J. C. (1980) *Cancer* 46, 2829–2834.
4. Manni, A., Arafah, B., and Pearson, O. H. (1980) *Cancer* 46, 2838–2841.
5. Jensen, E. V. (1981) *Cancer* 47, 2319–2326.
6. Iglehart, J. D. (1991) in: *Textbook of Surgery*, 14th edition, ed Sabiston, P. C. (W. B. Saunders, Philadelphia), pp. 510–550.
7. Ricketts, D., Turnbull, L., Ryall, G., Bakhshi, R., Rawson, N. S. B., Gazet, J. C., Nolan, C., & Coombes, R. C. (1991) *Cancer Res.* 51, 1817–1822.
8. Pike, M. C., Krailo, M. D., Henderson, B. E., Casagrande, J. T., and Hoel, D. G. (1983) *Nature* 303, 767–770.
9. Henderson, B. E., Ross, R. K., Judd, H. L., Krailo, M. D., and Pike, M. C. (1985) *Cancer* 56, 1206–1208.
10. Davis, D. L., Bradlow, H. L., Wolff, M., Woodruff, T., Hoel, D. G., and Anton-Culver, H. (1993) *Environ. Health Persp.* 101, 372–377.
11. Walter, P., Green, S., Greene, G., Krust, A., Bornert, J.-M., Jeltsch, J.-M., Staub, A., Jensen, E., Scrace, G., Waterfield, M., & Chambon, P. (1985) *Proc. Natl. Acad. Sci USA*, 82, 7889–7893.
12. Ponglikitmongkol, M., Green, S., & Chambon, P. (1988) *EMBO J.* 7, 3385–3388.
13. Kumar V., Green S., Stack G., Berry M., Jin J. R. & Chambon P. (1987) *Cell* 51, 941–951.
14. Tora, L., White, J., Brou, C., Tasset, D., Webster, N., Scheer, E. & Chambon, P. (1989) *Cell* 59, 477–478.
15. Danielian, P. S., White, R., Lees, J. A. & Parker, M. G. (1992) *EMBO J.* 11, 1025–1033.
16. Roodi, N., Bailey, L. R., Kao, W.-Y., Verrier, C. S., Yee, C. J., Dupont, W. D., & Parl, F. F. (1995) *J. of Natl Cancer Inst* 87, 446–451.
17. Lees, J. A., Fawell, S. E., White, R. & Parker, M. G. (1990) *Mol. Cell. Biol.* 10, 5529–5533.
18. Pfeffer, U., Fecarotta, E., Castagnetta, L., & Vidali, G. (1993) *Cancer Res.* 53, 741–743.
19. Zhang, Q.-X., Borg, A., & Fuqua, S. A. W. (1993) *Cancer Res.* 53, 5882–5884.
20. Castles, C. G., Fuqua, S. A. W., Klotz, D. M. & Hill, S. M. (1993) *Cancer Res.* 53, 5934–5939.
21. Miksicek, R. J. (1994) *Cancer Biology* 5, 369–379.
22. Pfeffer, U., Fecarotta, E., & Vidali, G. (1995) *Cancer Res.* 55, 2158–2165.

23. Fuqua, S. A. W. & Wolf, D. M. (1995) *Breast Cancer Res. and Treat.*, 35: 233–241.
24. Rea, D. & Parker, M. G. (1996) *Cancer Res.* 56: 1556–1563.
25. Fuqua, S. A. W., Fitzgerald, S. D., Chamness, G. C., Tandon, A. K., McDonnell, D. P., Nawaz, Z., O'Malley, B. W., & McGuire, W. L. (1991) *Cancer Res* 51, 105–109.
26. Daffada, A. A. I., Johnston, S. R. D., Smith, I. E., Detre, S., King, N., & Dowsett, M. (1995) *Cancer Res.* 55, 288–293.
27. Petersen, O. W., Høyer, P. E., & van Deurs, B. (1987) *Cancer Res* 47, 5748–5751.
28. Hammond, S. L., Ham, R. G. & Stampfer, M. R. (1984) *Proc. Natl. Acad. Sci. USA* 81, 5435–5439.
29. Band, V. & Sager, R. (1989) *Proc. Natl. Acad. Sci USA* 86, 1249–1253.
30. Kao, C.-Y., Nomata, K., Oakley, C. S., Welsch, C. W., & Chang, C.-C. (1995) *Carcinogenesis* 16, 531–538.
31. Chang, C.-C., Liu, C. J., Deocampo, N., Kang, K.-S., & Trosko, J. E. (1996) *Proceedings of the American Association for Cancer Research* 37, 38.
32. Kang K.-S., Wilson, M. R., Hayashi, T., Chang, C.-C. and Trosko, J. E. (1996) *Environ. Health Perspect.* 104, 192–200.
33. Nomata, K., Kang, K.-S., Hayashi, T., Matesic, D. F., Lockwood, B., Chang, C.-C., Trosko, J. E. (1996) *Cell Biology and Toxicology* 12, 69–78.
34. Ferguson, A. T., Lapidus, R. G., Baylin, S. B. & Davison, N. E. (1995) *Cancer Res* 55, 2279–2283.
35. Weigel, R. J., Crooks, D. L., Iglehart, D., & deconinck, E. C. (1995) *Cell Growth & Differentiation* 6, 707–711.
36. Liu, H., Wormkem M., Safe, S. H., & Bjeldanes L. F. (1994) *J. Natl.Cancer Inst.* 86, 1758–1765.
37. Johnston, S. R. D., Saccani-Jotti, G., Smith, I. E., Salter, J., Newby, J., Coppen, M., Ebbs, S. R., & Dowsett, M. (1995) *Cancer Res.* 55, 3331–3338.
38. Leygue, E. R., Watson, P. H., & Murphy, L. C. (1996) *J Natl Cancer Inst* 88, 284–296.
39. Wang, Y., and Miksicek, R. J. (1991) *Mol. Endocrinol* 5, 1707–1715.
40. Fuqua, S. A. W., Fizgerald, S. D., Allred, D. C., Elledge, R. M., Nawaz, Z., McDonnel, D. P., O'Malley, B. W., Greene, G. L. & McGuire, W. L. (1992) *Cancer Res.*, 52, 483–486.
41. Pfeffer, U., Fecarotta, E., Castagnetta, L., and Vidali, G. (1993) *Cancer Res.* 53, 741–743.
42. Fuqua, S. A. W., Alfred, D. C., Elledge, R. M., Elledge, R. M., Krieg, S. L., Benedix, M. G., Nawaz, Z., O'Malley, B. W., Greene, G. L. & McGuire, W. L. (1993) *Breast Cancer Res. Treat.* 26, 191–202.
43. Miksicek, R. J., Lei, Y., & Wang, Y. (1993) *Breast Cancer Res. Treat.* 26, 163–174.
44. Ray, A., Prefontaine, K. E. & Ray, P. (1994) *JBC* 269, 12940–12946.
45. Seol, W., Choi, H-S., Moore D. D. (1996) *Science* 272, 1336–1339.
46. Potter, V. R. (1978) *Br. J. Cancer* 38, 1–23.
47. Petersen, O. W., Ronnov-Jessen, L., Howlett, A. R., and Bissell, M. J. (1992). *Proc. Natl. Acad. sci. USA* 89; 9064–9068.
48. Yang, N. N., Venugopalan, M., Hardikar, S. and Glasebrook, A. (1996) *Science* 273, 1222–1225.

What is claimed is:

1. A substantially purified Type 1 human breast epithelial cell wherein the epithelial cell comprises the following characteristics:

(a) expresses a truncated human estrogen receptor having a molecular weight of approximately 48 kD,
   (b) proliferates in vitro in the presence of a medium comprising calcium chloride, sodium bicarbonate, sodium chloride, sodium phosphate, amino acids, glucose and sodium acetate, and
   (c) when cultured in vitro on a substratum comprising a matrix of reconstituted basement membrane components, forms budding and ductal structures, wherein said truncated human estrogen receptor binds to a monoclonal antibody recognizing the C-terminus of said truncated human estrogen receptor.

* * * * *

SEQUENCE LISTING

<160> NUMBER OF SEQ ID NOS: 7

<210> SEQ ID NO 1
<211> LENGTH: 20
<212> TYPE: DNA
<213> ORGANISM: Homo sapiens

<400> SEQUENCE: 1
gcaccctgaa gtctctggaa                                              20

<210> SEQ ID NO 2
<211> LENGTH: 20
<212> TYPE: DNA
<213> ORGANISM: Homo sapiens

<400> SEQUENCE: 2
tggctaaagt ggtgcatgat                                              20

<210> SEQ ID NO 3
<211> LENGTH: 20
<212> TYPE: DNA
<213> ORGANISM: Homo sapiens

<400> SEQUENCE: 3
tactgcatca gatccaaggg                                              20

<210> SEQ ID NO 4
<211> LENGTH: 20
<212> TYPE: DNA
<213> ORGANISM: Homo sapiens

-continued

```
<400> SEQUENCE: 4
atcaatggtg cactggttgg                                              20

<210> SEQ ID NO 5
<211> LENGTH: 20
<212> TYPE: DNA
<213> ORGANISM: Homo sapiens

<400> SEQUENCE: 5
atcaatggtg cactggttgg                                              20

<210> SEQ ID NO 6
<211> LENGTH: 24
<212> TYPE: DNA
<213> ORGANISM: Homo sapiens

<400> SEQUENCE: 6
agccttctcc atggtggtga agac                                         24

<210> SEQ ID NO 7
<211> LENGTH: 33
<212> TYPE: DNA
<213> ORGANISM: Homo sapiens

<400> SEQUENCE: 7
gtccaaagtc aggtcagtga cctgatcaaa gtt                               33
```